US010881350B2

(12) United States Patent
Lo et al.

(10) Patent No.: US 10,881,350 B2
(45) Date of Patent: Jan. 5, 2021

(54) PHYSIOLOGICAL SIGNAL MEASUREMENT DEVICE

(71) Applicant: Cheng Uei Precision Industry Co., Ltd., New Taipei (TW)

(72) Inventors: Sheng-Chieh Lo, New Taipei (TW); Peng-Yuan Lee, New Taipei (TW); Chih-Yuan Lu, New Taipei (TW)

(73) Assignee: CHENG UEI PRECISION INDUSTRY CO., LTD., New Taipei (TW)

( * ) Notice: Subject to any disclaimer, the term of this patent is extended or adjusted under 35 U.S.C. 154(b) by 367 days.

(21) Appl. No.: 15/975,645

(22) Filed: May 9, 2018

(65) Prior Publication Data
US 2019/0343460 A1 Nov. 14, 2019

(51) Int. Cl.
A61B 5/00 (2006.01)
H05K 5/00 (2006.01)
(Continued)

(52) U.S. Cl.
CPC .......... *A61B 5/6817* (2013.01); *A61B 5/0084* (2013.01); *H05K 1/028* (2013.01); *H05K 1/14* (2013.01); *H05K 1/18* (2013.01); *H05K 5/0086* (2013.01); *H05K 5/0091* (2013.01); *H05K 5/03* (2013.01); *H05K 7/1427* (2013.01);
(Continued)

(58) Field of Classification Search
CPC ............... A61B 5/6817; A61B 5/0084; A61B 2562/166; A61B 2562/0233; A61B 2562/04; A61B 2562/164; A61B 2560/0214; A61B 5/14551; A61B 5/02438; A61B 5/02416; A61B 5/6803; H05K 5/0086; H05K 7/1427; H05K 1/14; H05K 1/028; H05K 1/18; H05K 5/03; H05K 5/0091; H05K 2201/10151; H05K 2201/10121; H05K 2201/10037; H05K 2201/10083; H05K 1/147; H05K 2201/10106
USPC ....... 600/300, 301, 309, 310, 322–328, 332, 600/339, 476–479
See application file for complete search history.

(56) References Cited

U.S. PATENT DOCUMENTS

2015/0032009 A1* 1/2015 LeBoeuf ............ A61B 5/14551
600/476
2015/0257662 A1* 9/2015 Lee .................... A61B 5/02405
600/323

FOREIGN PATENT DOCUMENTS

CN            205754761 U  * 11/2016  .......... A61B 5/6803

* cited by examiner

Primary Examiner — Jeffrey G Hoekstra
Assistant Examiner — Renee C Langhals
(74) Attorney, Agent, or Firm — Cheng-Ju Chiang

(57) ABSTRACT

A physiological signal measurement device includes a housing, a bracket, a rigid circuit board fastened in the housing, a first flexible circuit board assembled in the housing and the in-ear portion, and a protective sleeve. The housing protrudes frontward to form an in-ear portion. The bracket has a base portion fastened to the in-ear portion. Several portions of a front surface of the base portion protrude frontward to form a plurality of first elastic portions. The first flexible circuit board has a resilient end. The resilient end of the first flexible circuit board surrounds the plurality of the first elastic portions. The protective sleeve has a fastening portion, and a plurality of spaced second elastic portions protruded from the fastening portion. The plurality of the (Continued)

spaced second elastic portions surround the plurality of the first elastic portions and the resilient end of the first flexible circuit board.

16 Claims, 7 Drawing Sheets

(51) Int. Cl.
*H05K 7/14* (2006.01)
*H05K 1/14* (2006.01)
*H05K 1/02* (2006.01)
*H05K 1/18* (2006.01)
*H05K 5/03* (2006.01)

(52) U.S. Cl.
CPC .................. *A61B 2560/0214* (2013.01); *A61B 2562/0233* (2013.01); *A61B 2562/04* (2013.01); *A61B 2562/164* (2013.01); *A61B 2562/166* (2013.01); *H05K 2201/10037* (2013.01); *H05K 2201/10121* (2013.01); *H05K 2201/10151* (2013.01)

PHYSIOLOGICAL SIGNAL MEASUREMENT DEVICE

BACKGROUND OF THE INVENTION

1. Field of the Invention

The present invention generally relates to a measurement device, and more particularly to a physiological signal measurement device.

2. The Related Art

Conventionally, various different measurement devices are needed for proceeding measuring physiological data of human body. In order to make people be capable of knowing the physiological data of the human body anywhere at any time, the various different measurement devices are developed towards a miniaturization direction or integrated in other electronic devices.

In order to promote usage rates and applicabilities of the various different measurement devices, a conventional physiological signal measurement device is disposed to an earphone for measuring vessels of an auricle of a user, so that various physiological data of the user, such as heart rate data, heart rate variability data or other data are calculated. The conventional physiological signal measurement device includes a light emitter, a light sensor, and a microprocessor electrically connected with the light emitter and the light sensor. The light emitter emits a light source to skin of the auricle of the user. The light sensor receives a light source emitted from the light emitter and reflected by the skin of the auricle of the user for a while to draw a group of continuous varying waveforms and transmit the group of the continuous varying waveforms to a microprocessor. The microprocessor cooperates with an analytical method of the various physiological data to record variations of physiological statuses of the user per unit time.

However, when the user uses the conventional physiological signal measurement device, external light rays will also shine on the skin of the auricle of the user, the light source received by the light sensor will suffer interferences of the external light rays that makes the data measured by the conventional physiological signal measurement device inaccurate.

Thus, in order to overcome the above-mentioned problems, an innovative physiological signal measurement device is essential to be provided, the innovative physiological signal measurement device is capable of avoiding suffering the interferences of the external light rays and making data measured by the innovative physiological signal measurement device accurate.

SUMMARY OF THE INVENTION

An object of the present invention is to provide a physiological signal measurement device. The physiological signal measurement device includes a housing, a bracket, a rigid circuit board, a first flexible circuit board and a protective sleeve. A front surface of the housing protrudes frontward to form a hollow in-ear portion. The bracket has a base portion fastened to a front end of the in-ear portion. Several portions of a front surface of the base portion protrude frontward to form a plurality of first elastic portions arranged in a ring shape. The rigid circuit board is fastened in the housing. The rigid circuit board is equipped with a microprocessor. The first flexible circuit board is assembled in the housing and the in-ear portion. The first flexible circuit board has a fastening end and a resilient end. The fastening end of the first flexible circuit board is electrically connected with the rigid circuit board. The resilient end of the first flexible circuit board projects beyond the front surface of the base portion and surrounds the plurality of the first elastic portions. An outside of the resilient end of the first flexible circuit board is equipped with a plurality of light emitters and a plurality of light sensors. Each of the plurality of the first elastic portions is corresponding to one of the plurality of the light emitters and one of the plurality of the light sensors. The plurality of the light emitters and the plurality of the light sensors of the first flexible circuit board are electrically connected with the microprocessor of the rigid circuit board by virtue of the first flexible circuit board. The protective sleeve has a fastening portion, and a plurality of spaced second elastic portions protruded from a front surface of the fastening portion and arranged in a ring shape. The fastening portion is fastened to root portions of outer sides of the plurality of the first elastic portions. The plurality of the spaced second elastic portions surround free ends of the plurality of the first elastic portions and the outside of the resilient end of the first flexible circuit board. The plurality of the light emitters and the plurality of the light sensors are clamped between the plurality of the first elastic portions and the plurality of the spaced second elastic portions.

As described above, when the physiological signal measurement device is in use, the plurality of the first elastic portions and the plurality of the spaced second elastic portions all stretch into an external auditory canal of a user by virtue of the plurality of the light emitters and the plurality of the light sensors of the first flexible circuit board of the physiological signal measurement device are clamped between the plurality of the first elastic portions and the plurality of the spaced second elastic portions, the plurality of the first elastic portions occur an inward slight deformation by virtue of skin of the external auditory canal pushing against the plurality of the spaced second elastic portions to make the plurality of the first elastic portions and the plurality of the spaced second elastic portions generate an outward pushing force, so that an outer surface of each of the plurality of the spaced second elastic portions is neatly adhered to the skin of the external auditory canal, after the plurality of the first elastic portions occur the deformation, a distance between the skin of the external auditory canal, and the plurality of the light emitters and the plurality of the light sensors of the first flexible circuit board is still kept being constant, various physiological data measured by the physiological signal measurement device are ensured to be accurate, in addition, the plurality of the light emitters of the first flexible circuit board emit light sources to shine the skin of the external auditory canal, the plurality of the light sensors are capable of avoiding interferences of external light rays at the time of the plurality of the light sensors receiving reflected light sources reflected by the skin of the external auditory canal, so that the various physiological data measured by the physiological signal measurement device are further ensured to be accurate.

BRIEF DESCRIPTION OF THE DRAWINGS

The present invention will be apparent to those skilled in the art by reading the following description, with reference to the attached drawings, in which.

DETAILED DESCRIPTION OF THE PREFERRED EMBODIMENT

Figure 1:
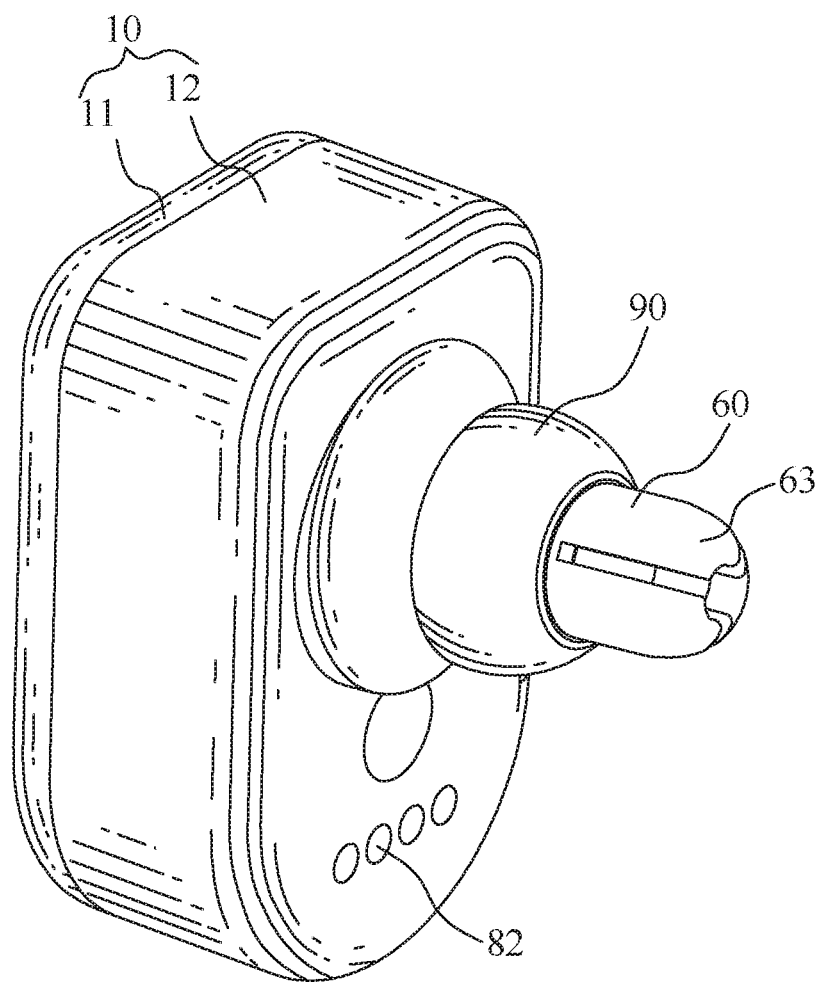
FIG. 1 is a perspective view of a physiological signal measurement device in accordance with a preferred embodiment of the present invention.
Figure 2:
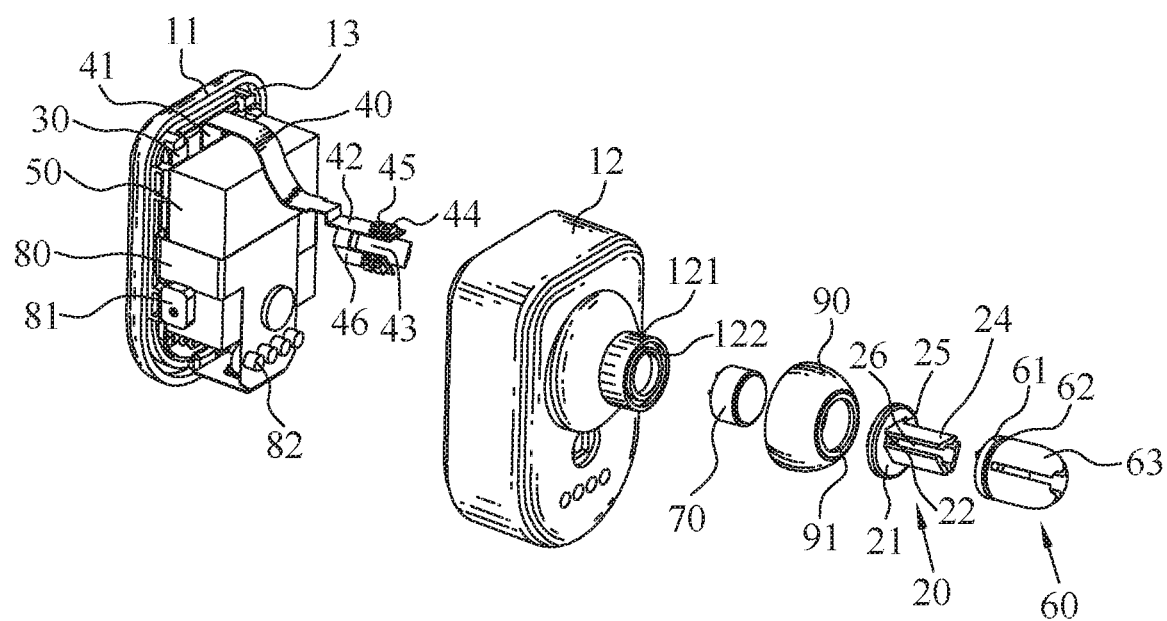
FIG. 2 is an exploded perspective view of the physiological signal measurement device of FIG. 1.

With reference to FIG. 1 and FIG. 2, a physiological signal measurement device 100 in accordance with a preferred embodiment of the present invention is shown. The physiological signal measurement device 100 is a Bluetooth earphone having a physiological signal measurement function. The physiological signal measurement device 100 includes a housing 10, a bracket 20, a rigid circuit board 30, a first flexible circuit board 40, a battery 50, a protective sleeve 60, a loudspeaker 70, a second flexible circuit board 80 and an earplug 90.

Referring to FIG. 1 and FIG. 2 again, the housing 10 includes a rear cover 11, and a front cover 12 covered to a front end of the rear cover 11. A front surface of the housing 10 protrudes frontward to form a hollow cylinder-shaped in-ear portion 121. After the front cover 12 is covered to the rear cover 11, a receiving chamber 13 is formed between the front cover 12 and the rear cover 11. A front of the front cover 12 opens a through-hole 123 communicated between an outside and an inside of the front cover 12. The front of the front cover 12 protrudes frontward to form the hollow cylinder-shaped in-ear portion 121 located in front of and communicated with the through-hole 123. Specifically, a front surface of a peripheral wall of the through-hole 123 protrudes frontward to form the in-ear portion 121. A front surface of the in-ear portion 121 opens an annular assembling slot 122.

Figure 3:
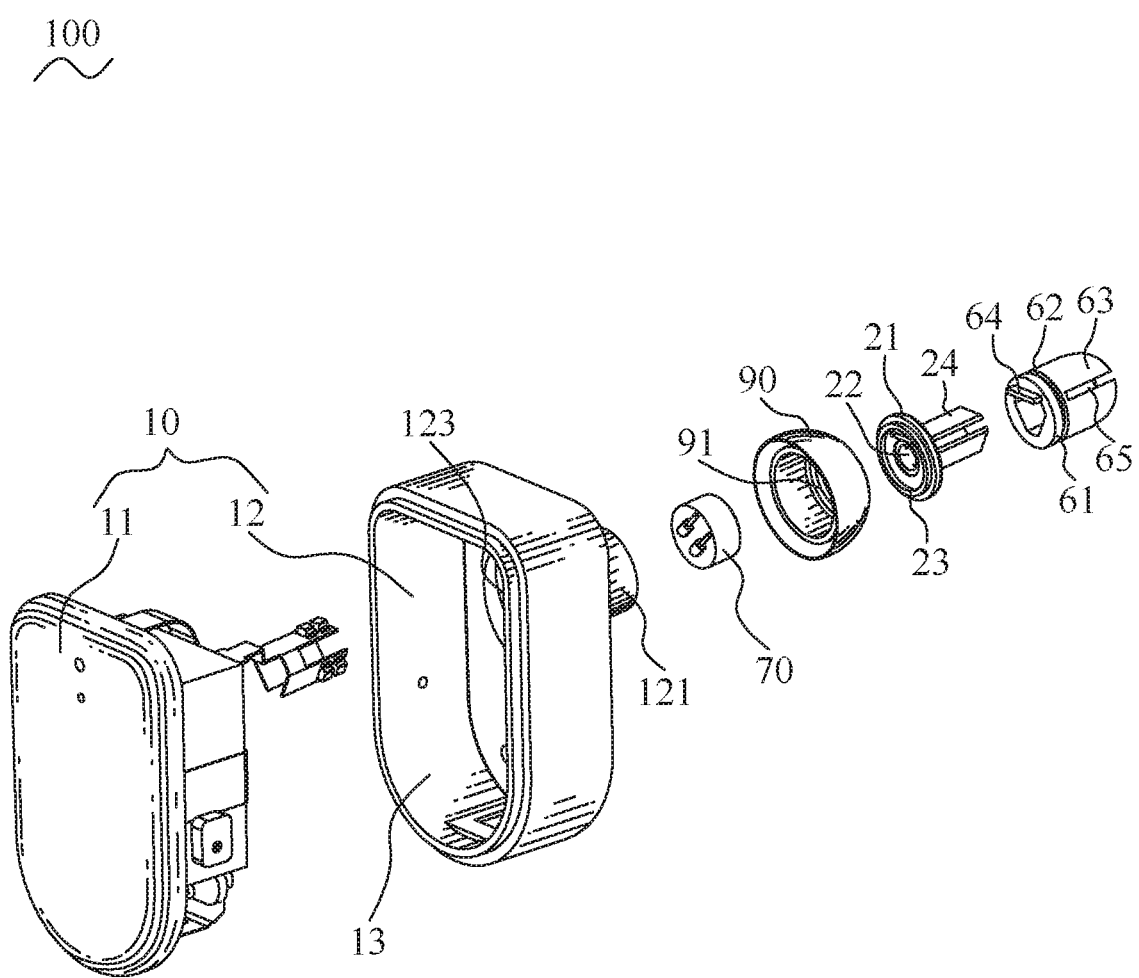
FIG. 3 is another exploded perspective view of the physiological signal measurement device of FIG. 1.
Figure 4:
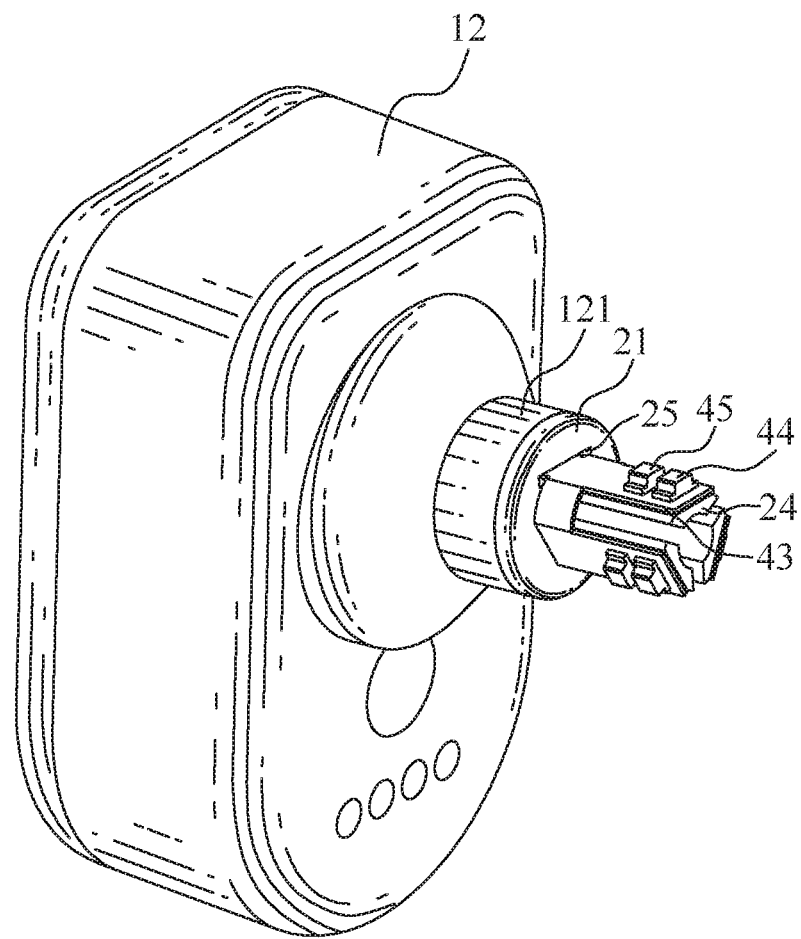
FIG. 4 is a partially perspective view of the physiological signal measurement device of FIG. 1, wherein an earplug and a protective sleeve are omitted.
Figure 5:
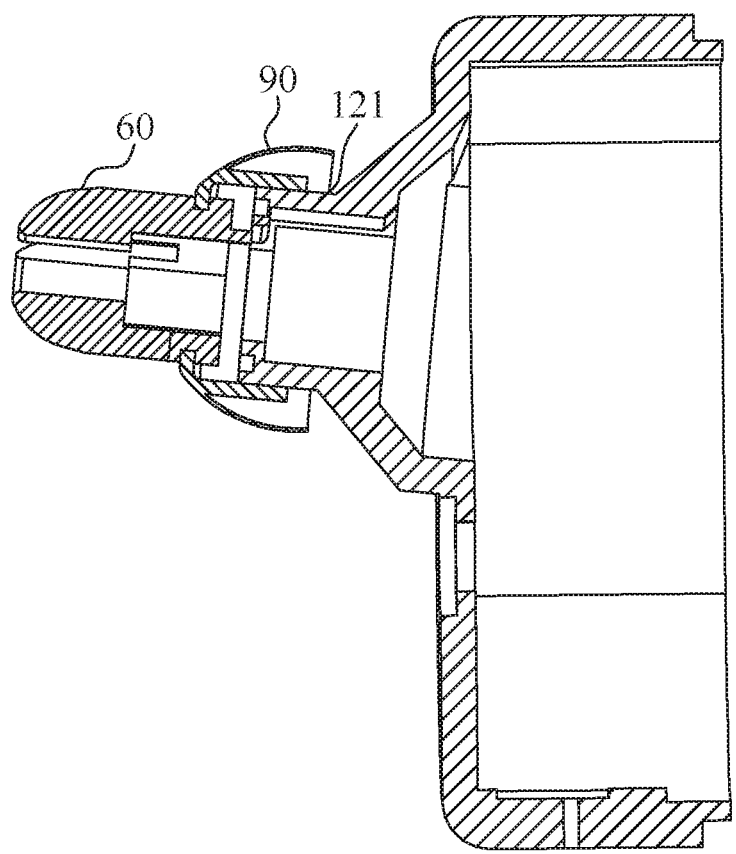
FIG. 5 is a partially sectional view of the physiological signal measurement device of FIG. 1.
Figure 6:
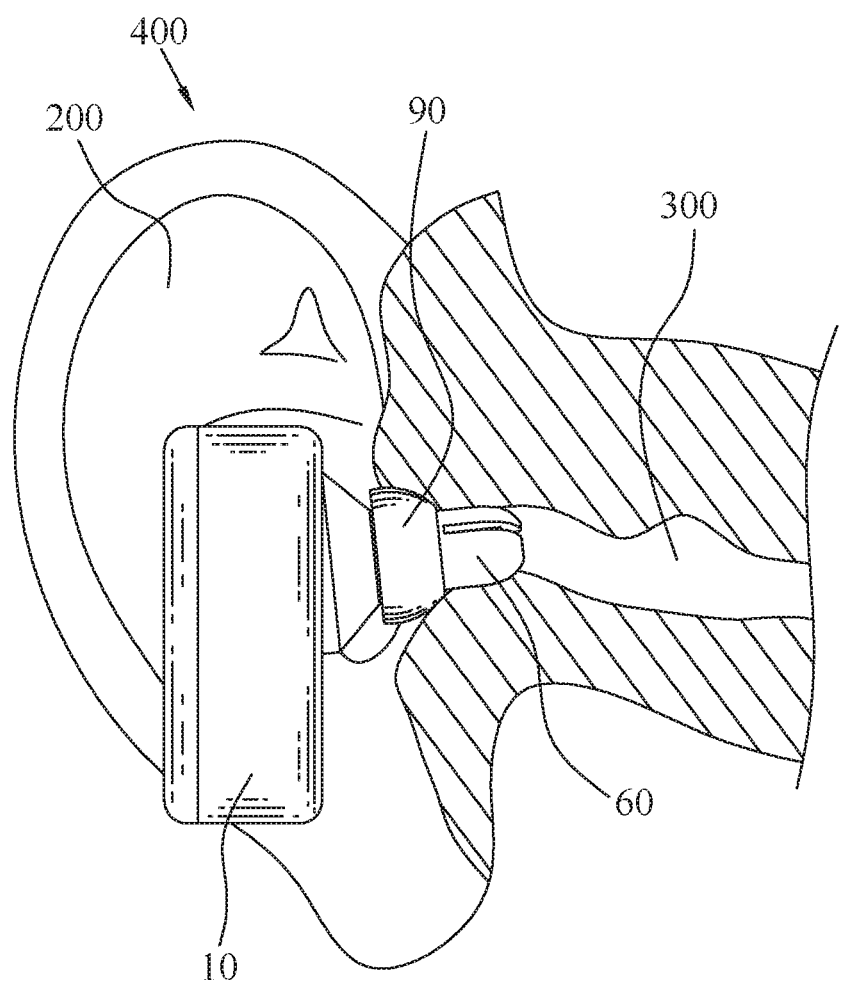
FIG. 6 is a diagrammatic drawing of the physiological signal measurement device of FIG. 1, wherein the physiological signal measurement device is worn in an ear of a user.

Referring to FIG. 2 and FIG. 3, the bracket 20 has a base portion 21. A middle of the base portion 21 opens a sound hole 22. A periphery of a rear surface of the base portion 21 protrudes rearward to form a ring-shaped assembling block 23. Several portions of a front surface of the base portion 21 protrude frontward to form a plurality of first elastic portions 24 arranged in a ring shape. Each two of the plurality of the first elastic portions 24 are spaced from each other to form a gap 26. Specifically, the plurality of the first elastic portions 24 are arranged around the sound hole 22. The base portion 21 opens a rectangular opening 25 corresponding to an outer side of one of the plurality of the first elastic portions 24. The base portion 21 is fastened to a front end of the in-ear portion 121. Specifically, the assembling block 23 is fastened in the assembling slot 122 of the in-ear portion 121.

Figure 7:
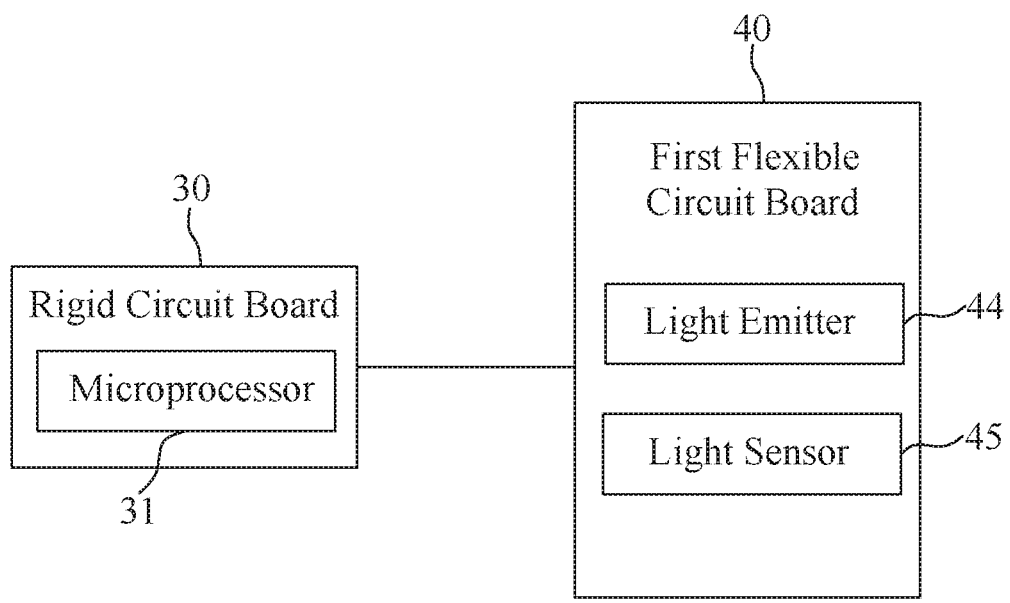
FIG. 7 is a partial block diagram of the physiological signal measurement device of FIG. 1.

Referring to FIG. 2, FIG. 3 and FIG. 7, the rigid circuit board 30 is fastened in the receiving chamber 13 of the housing 10. The rigid circuit board 30 is equipped with a microprocessor 31 and a wireless transmission module (not shown).

Referring to FIG. 1 to FIG. 7, the first flexible circuit board 40 is assembled in the receiving chamber 13 of the housing 10 and the in-ear portion 121. The first flexible circuit board 40 has a fastening end 41 and a resilient end 42. The fastening end 41 of the first flexible circuit board 40 is electrically connected with the rigid circuit board 30. The resilient end 42 of the first flexible circuit board 40 has a plurality of protruding portions 46. Each of the plurality of the protruding portions 46 are spaced from each other to form a notch 43. The plurality of the protruding portions 46 surround a substantially barrel shape. The resilient end 42 of the first flexible circuit board 40 passes through the opening 25. The resilient end 42 of the first flexible circuit board 40 projects beyond the front surface of the base portion 21 and surrounds the plurality of the first elastic portions 24. The resilient end 42 of the first flexible circuit board 40 is disposed to the outer sides of the plurality of the first elastic portions 24. Specifically, one of the plurality of the protruding portions 46 passes through the opening 25. The plurality of the protruding portions 46 project beyond the front surface of the base portion 21 and are separately disposed to the outer sides of the plurality of the first elastic portions 24. The gap 26 of each two first elastic portions 24 is corresponding to one of the plurality of the notches 43. An outside of the resilient end 42 of the first flexible circuit board 40 is equipped with a plurality of light emitters 44 and a plurality of light sensors 45. Each of the plurality of the first elastic portions 24 is corresponding to one of the plurality of the light emitters 44 and one of the plurality of the light sensors 45. Two portions of an outer surface of each of the plurality of the protruding portions 46 of the first flexible circuit board 40 separately corresponding to the plurality of the first elastic portions 24 are equipped with the one of the plurality of the light emitters 44 and the one of the plurality of the light sensors 45. The plurality of the light emitters 44 and the plurality of the light sensors 45 of the first flexible circuit board 40 are electrically connected with the microprocessor 31 of the rigid circuit board 30 by virtue of the first flexible circuit board 40.

Referring to FIG. 2 and FIG. 3, the battery 50 is assembled in the receiving chamber 13 of the housing 10 and is disposed to a front surface of the rigid circuit board 30. The battery 50 is electrically connected with the rigid circuit board 30 for providing a power source needed by the physiological signal measurement device 100 in accordance with the present invention.

Referring to FIG. 1 to FIG. 4 again, the protective sleeve 60 is made of transparent soft material. The transparent soft material is soft rubber or soft plastic. The protective sleeve 60 has a fastening portion 61, and a plurality of spaced second elastic portions 63 protruded from a front surface of the fastening portion 61 and arranged in a ring shape. A rear end of an outer peripheral surface of the fastening portion 61 opens a ring-shaped wedging slot 62 for assembling the earplug 90. The protective sleeve 60 is formed by an integrated molding technology. The fastening portion 61 is fastened to root portions of the outer sides of the plurality of the first elastic portions 24. The protective sleeve 60 is of a hollow bullet shape. An interval 65 is formed between each two of the plurality of the spaced second elastic portions 63. The protective sleeve 60 surrounds the bracket 20 and the resilient end 42 of the first flexible circuit board 40. The plurality of the spaced second elastic portions 63 surround free ends of the plurality of the first elastic portions 24 and the outside of the resilient end 42 of the first flexible circuit board 40. The plurality of the spaced second elastic portions 63 surround the plurality of the protruding portions 46. The plurality of the spaced second elastic portions 63 are corresponding to the plurality of the first elastic portions 24 separately and are corresponding to the plurality of the protruding portions 46 separately. The interval 65 of each two spaced second elastic portions 63 is corresponding to the gap 26 of two of the plurality of the first elastic portions 24 and the notch 43 of two of the plurality of the protruding portions 46. The plurality of the light emitters 44 and the plurality of the light sensors 45 of the first flexible circuit board 40 are clamped between the plurality of the first elastic portions 24 and the plurality of the spaced second elastic portions 63. The protective sleeve 60 further includes a fastening block 64 molded with a rear surface of the fastening portion 61. The fastening block 64 surrounds an outer side of the first flexible circuit board 40. Specifically, the fastening block 64 surrounds the one of the plurality of the protruding portions 46 and is received in the opening 25.

Referring to FIG. 1, FIG. 2 FIG. 3 and FIG. 5, the loudspeaker 70 is assembled in the in-ear portion 121 and is electrically connected with the rigid circuit board 30 by virtue of an electric wire (not shown). The second flexible circuit board 80 is assembled in the receiving chamber 13 of the housing 10 and is disposed to a bottom surface of the battery 50. The second flexible circuit board 80 is electrically connected with the rigid circuit board 30. The second flexible circuit board 80 is equipped with at least one microphone 81. The second flexible circuit board 80 further includes a plurality of external terminals 82. The plurality of the external terminals 82 are all exposed to a lower portion of a front surface of the front cover 12 of the housing 10. The plurality of the external terminals 82 are connected with docking terminals (not shown) and are capable of being used for transmitting electrical signals or transmitting the power source at the time of charging the physiological signal measurement device 100.

The earplug 90 is of a hollow hemisphere shape. A rear end of the earplug 90 is wider than a front end of the earplug 90. A peripheral surface of the earplug 90 is gradually indented inward towards a center of the earplug 90 from the rear end of the earplug 90 to the front end of the earplug 90. The earplug 90 is mounted outside the in-ear portion 121 and one end of the fastening portion 61 of the protective sleeve 60 adjacent to the in-ear portion 121. Specifically, a front of an inner periphery of the earplug 90 protrudes inward towards the center of the earplug 90 to form a ring-shaped wedging portion 91. The wedging portion 91 is wedged in the wedging slot 62.

Referring to FIG. 1 to FIG. 6, when the physiological signal measurement device 100 is worn, the housing 10 is worn to an auricle 200 of a user 400, the earplug 90 abuts against an inner wall of an entrance of an external auditory canal 300 and the auricle 200, so that light of an external environment is shielded to enter the external auditory canal 300 and a position of wearing the physiological signal measurement device 100 is limited. The earplug 90 is also capable of obstructing noises of the external environment to make the physiological signal measurement device 100 undisturbed by the external environment. When the physiological signal measurement device 100 is in use, the plurality of the first elastic portions 24, the resilient end 42 of the first flexible circuit board 40 and the plurality of the spaced second elastic portions 63 all stretch into the external auditory canal 300 of the user 400, the plurality of the first elastic portions 24 occur an inward slight deformation by virtue of skin of the external auditory canal 300 pushing against the plurality of the spaced second elastic portions 63 to make the plurality of the first elastic portions 24 and the plurality of the spaced second elastic portions 63 generate an outward pushing force, so that an outer surface of each of the plurality of the spaced second elastic portions 63 is neatly adhered to the skin of the external auditory canal 300. After the plurality of the first elastic portions 24 occur the deformation, a distance between the skin of the external auditory canal 300, and the plurality of the light emitters 44 and the plurality of the light sensors 45 of the first flexible circuit board 40 is still kept being constant, consequently, various physiological data measured by the physiological signal measurement device 100 are ensured to be accurate.

A working principle of the physiological signal measurement device 100 is described as follows. Turn on a switch, the plurality of the light emitters 44 of the first flexible circuit board 40 all emit light sources penetrating through the plurality of the spaced second elastic portions 63 to shine the skin of the external auditory canal 300. The light sources are reflected by the skin of the external auditory canal 300 for a while. The plurality of the light sensors 45 separately receive the reflected light sources reflected by the skin of the external auditory canal 300 within a period of time, a group of continuously variable waveforms are drawn and the group of the continuously variable waveforms are transmitted to the microprocessor 31. The plurality of the light sensors 45 are capable of avoiding interferences of external light rays at the time of the plurality of the light sensors 45 receiving the reflected light sources reflected by the skin of the external auditory canal 300. The microprocessor 31 cooperates an analytical method of the various physiological data measured by the physiological signal measurement device 100, physiologic variations of the user 400 per unit time are recorded and are transmitted to a display device (not shown) by virtue of the external terminals 82 or the wireless transmission module. The display device is an intelligent cell phone, an intelligent watch or etc. The various physiological data include heart rate data, heart rate variability data, oxyhemoglobin saturation data and other physiological data of a human body.

As described above, when the physiological signal measurement device 100 is in use, the plurality of the first elastic portions 24 and the plurality of the spaced second elastic portions 63 all stretch into the external auditory canal 300 of the user 400 by virtue of the plurality of the light emitters 44 and the plurality of the light sensors 45 of the first flexible circuit board 40 of the physiological signal measurement device 100 are clamped between the plurality of the first elastic portions 24 and the plurality of the spaced second elastic portions 63, the plurality of the first elastic portions 24 occur the inward slight deformation by virtue of the skin of the external auditory canal 300 pushing against the plurality of the spaced second elastic portions 63 to make the plurality of the first elastic portions 24 and the plurality of the spaced second elastic portions 63 generate the outward pushing force, so that the outer surface of each of the plurality of the spaced second elastic portions 63 is neatly adhered to the skin of the external auditory canal 300, after the plurality of the first elastic portions 24 occur the deformation, a distance between the skin of the external auditory canal 300, and the plurality of the light emitters 44 and the plurality of the light sensors 45 of the first flexible circuit board 40 is still kept being constant, the various physiological data measured by the physiological signal measurement device 100 are ensured to be accurate, in addition, the plurality of the light emitters 44 of the first flexible circuit board 40 emit the light sources to shine the skin of the external auditory canal 300, the plurality of the light sensors 45 are capable of avoiding the interferences of the external light rays at the time of the plurality of the light sensors 45 receiving the reflected light sources reflected by the skin of the external auditory canal 300, so that the various physiological data measured by the physiological signal measurement device 100 are further ensured to be accurate.

What is claimed is:

1. A physiological signal measurement device, comprising:
   a housing, a front surface of the housing protruding frontward to form a hollow in-ear portion;
   a bracket having a base portion fastened to a front end of the in-ear portion, several portions of a front surface of the base portion protruding frontward to form a plurality of first elastic portions arranged in a ring shape;
   a rigid circuit board fastened in the housing, the rigid circuit board being equipped with a microprocessor;
   a first flexible circuit board assembled in the housing and the in-ear portion, the first flexible circuit board having a fastening end and a resilient end, the fastening end of the first flexible circuit board being electrically connected with the rigid circuit board, the resilient end of the first flexible circuit board projecting beyond the front surface of the base portion and surrounding the plurality of the first elastic portions, an outside of the resilient end of the first flexible circuit board being equipped with a plurality of light emitters and a plurality of light sensors, each of the plurality of the first elastic portions being corresponding to one of the plurality of the light emitters and one of the plurality of the light sensors, the plurality of the light emitters and the plurality of the light sensors of the first flexible circuit board being electrically connected with the microprocessor of the rigid circuit board by virtue of the first flexible circuit board; and
   a protective sleeve having a fastening portion, and a plurality of spaced second elastic portions protruded from a front surface of the fastening portion and arranged in a ring shape, the fastening portion being fastened to root portions of outer sides of the plurality of the first elastic portions, the plurality of the spaced second elastic portions surrounding free ends of the plurality of the first elastic portions and the outside of the resilient end of the first flexible circuit board, the plurality of the light emitters and the plurality of the light sensors being clamped between the plurality of the first elastic portions and the plurality of the spaced second elastic portions.

2. The physiological signal measurement device as claimed in claim 1, wherein the resilient end of the first flexible circuit board has a plurality of protruding portions, each of the plurality of the protruding portions are spaced from each other to form a notch.

3. The physiological signal measurement device as claimed in claim 2, wherein the plurality of the protruding portions surround a substantially barrel shape.

4. The physiological signal measurement device as claimed in claim 2, wherein the base portion opens an opening corresponding to an outer side of one of the plurality of the first elastic portions, one of the plurality of the protruding portions passes through the opening, the plurality of the protruding portions project beyond the front surface of the base portion and are separately disposed to the outer sides of the plurality of the first elastic portions.

5. The physiological signal measurement device as claimed in claim 2, wherein the plurality of the spaced second elastic portions surround the plurality of the protruding portions, the plurality of the spaced second elastic portions are corresponding to the plurality of the first elastic portions separately and are corresponding to the plurality of the protruding portions separately.

6. The physiological signal measurement device as claimed in claim 1, wherein a front surface of the in-ear portion opens an assembling slot, a periphery of a rear surface of the base portion protrudes rearward to form an assembling block, the assembling block is fastened in the assembling slot.

7. The physiological signal measurement device as claimed in claim 1, wherein the housing includes a rear cover, and a front cover covered to a front end of the rear cover, a front of the front cover opens a through-hole communicated between an outside and an inside of the front cover, the front of the front cover protrudes frontward to form the hollow cylinder-shaped in-ear portion located in front of and communicated with the through-hole.

8. The physiological signal measurement device as claimed in claim 7, wherein a front surface of a peripheral wall of the through-hole protrudes frontward to form the in-ear portion.

9. The physiological signal measurement device as claimed in claim 7, wherein after the front cover is covered to the rear cover, a receiving chamber is formed between the front cover and the rear cover, the rigid circuit board is fastened in the receiving chamber of the housing.

10. The physiological signal measurement device as claimed in claim 7, further comprising a battery and a second flexible circuit board, the second flexible circuit board being disposed to a bottom surface of the battery, the battery and the second flexible circuit board being assembled in the receiving chamber.

11. The physiological signal measurement device as claimed in claim 1, further comprising a battery, the battery being assembled in the housing, the battery being electrically connected with the rigid circuit board.

12. The physiological signal measurement device as claimed in claim 11, wherein the battery is disposed to a front surface of the rigid circuit board.

13. The physiological signal measurement device as claimed in claim 1, further comprising a second flexible circuit board, the second flexible circuit board being assembled in the housing, the second flexible circuit board being electrically connected with the rigid circuit board, the second flexible circuit board being equipped with at least one microphone.

14. The physiological signal measurement device as claimed in claim 13, wherein the second flexible circuit board further includes a plurality of external terminals, the plurality of the external terminals are all exposed to the housing.

15. The physiological signal measurement device as claimed in claim 1, further comprising a loudspeaker assembled in the in-ear portion and electrically connected with the rigid circuit board, a middle of the base portion opening a sound hole, the plurality of the first elastic portions being arranged around the sound hole.

16. The physiological signal measurement device as claimed in claim 1, further comprising an earplug of a hollow hemisphere shape, a rear end of the earplug being wider than a front end of the earplug, the earplug being mounted outside the in-ear portion and one end of the fastening portion of the protective sleeve adjacent to the in-ear portion.

\* \* \* \* \*